United States Patent [19]
Stark

[11] Patent Number: 5,953,097
[45] Date of Patent: *Sep. 14, 1999

[54] CONTACT LENS FOR USE WITH OPHTHALMIC MONITORING SYSTEMS

[75] Inventor: Lawrence W. Stark, Berkeley, Calif.

[73] Assignee: Neuroptics, Inc., Huntington Beach, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/880,301

[22] Filed: Jun. 24, 1997

[51] Int. Cl.⁶ .............................. G02C 7/04; A61B 3/00
[52] U.S. Cl. .................................... 351/160 R; 351/219
[58] Field of Search ....................... 351/160 R, 160 H, 351/161, 162, 219

[56] References Cited

U.S. PATENT DOCUMENTS

| | | | |
|---|---|---|---|
| 3,929,124 | 12/1975 | Yablonski et al. | 600/489 |
| 4,007,980 | 2/1977 | Bracher et al. | 351/219 |
| 4,966,452 | 10/1990 | Shields et al. | 351/160 R |
| 5,022,749 | 6/1991 | Ogura | 351/219 |
| 5,200,773 | 4/1993 | Volk | 351/219 |
| 5,297,554 | 3/1994 | Glynn et al. | 600/476 |
| 5,608,472 | 3/1997 | Szirth et al. | 351/206 |

Primary Examiner—Georgia Epps
Assistant Examiner—Jordan M. Schwartz
Attorney, Agent, or Firm—Lyon & Lyon LLP

[57] ABSTRACT

A contact lens for use with pupil monitoring systems. A contact lens has a first surface that conforms to a cornea and sclera of patient's eye, and a second surface that has a tubular extension defining a viewing port formed thereon. A distal region of the tubular extension forms an outwardly protruding lip which functions to securely engage the eyelid of a patient during the monitoring process and facilitates manipulation of the scleral contact lens while it is being inserted in or removed from a patient's eye. The lens may conform solely to the cornea of a patient's eye, and the viewing port may have a wide angle lens, polarizing element or other optical filtering element provided therein.

15 Claims, 4 Drawing Sheets

CONTACT LENS FOR USE WITH OPHTHALMIC MONITORING SYSTEMS

BACKGROUND OF THE INVENTION

The field of the present invention is ophthalmic monitoring systems and, more particularly, scleral and corneal contact lenses for use with such systems.

Recently, substantial attention has been directed to the use of pupil monitoring systems for use in medical applications. One such system is described in U.S. Pat. No. 5,297,554, which is entitled "Device for Use in Real-Time Monitoring of Human or Animal Bodily Function" (hereinafter "the '554 patent"). The system described in the '554 patent employs a scleral contact lens for locating and supporting on the eye of a patient an optical system including at least one discrete light source and one discrete receiver. The described scleral contact lens has a first surface which conforms to the sclera and bulbar conjunctive tissue of a patient's eye, and a second surface including a tubular extension that provides a mount for the optical system.

While the system described in the '554 patent may be useful in short term pupil monitoring applications, its usefulness for long term pupil monitoring applications is questionable. The reason for this is that the combination of the scleral contact lens and optical monitoring system is quite bulky. Moreover, it is difficult to assess how long a patient's eye could tolerate having a device such as that described in the '554 patent mounted thereon.

Another device for monitoring the size of a patient's pupil is described in U.S. Pat. No. 4,007,980, entitled "Device for the Measurement of the Size of an Eye Pupil" (hereinafter "the '980 patent"). The device described in the '980 patent is also quite bulky and likely could not be tolerated by a patient's eye for substantial periods of time.

In view of the foregoing, it is believed that those skilled in the art would find a scleral contact lens that could be easily manipulated and left on a patient's eye for a substantial period of time to be quite useful.

SUMMARY OF THE INVENTION

The present invention is directed to a contact lens that may be easily manipulated, may be left on a patient's eye for substantial periods of time, provides a means for calibration and evaluation of eye rotation during monitoring, and provides a reliable means for keeping the eyelid of a patient open during the monitoring process.

In one innovative aspect, the present invention is directed to a scleral contact lens that has a first (or back) surface generally conforming to the cornea and sclera of a patient's eye, and a second (or front) surface that forms a tubular viewing port. In a preferred form, the portion of the first surface that conforms to the sclera of a patient's eye is adapted to rest on the sclera, while the portion that conforms to the cornea is slightly separated from the cornea. A distal portion of the tubular viewing port forms an outwardly protruding lip from a visual axis. The outwardly protruding lip functions to hold the eyelid of a patient open during the pupil monitoring process, facilitates manipulation of the scleral contact lens while it is being inserted in or removed from the patient's eye, and allows the tubular viewing port to provide maximum visibility within an eye by minimizing the distance that the tubular viewing port extends outwardly from the eye.

In a preferred form, a plurality of fiduciary points may be provided along an upper surface of the outwardly protruding lip of the contact lens and may be used as a means for calibrating an associated ophthalmic monitoring system, locating the contact lens in three dimensional space, and/or determining an amount of rotation of an eye during, for example, pupil, retina or other ocular tissue or vessel monitoring processes. The fiduciary points may take numerous forms including, for example, colored shapes or textured areas.

In other innovative aspects, the back surface of the contact lens may conform solely to the cornea of a patient's eye, thus minimizing the size of the overall lens, and the tubular viewing port may be flared outwardly, thus eliminating a need for the outwardly protruding lip described above.

In still another innovative aspect, a contact lens in accordance with the present invention may include a viewing port that includes a wide angle lens, and enables measurement of a pupil diameter up to, for example, 11 mm. If desired, a gonioscopic lens, a polarizing element or film or some other type of optical light filter may also be included in the viewing port.

Finally, in still another innovative aspect, the scleral contact lens of the present invention may be designed to function as a bandage lens and to protect the patient's eye during ophthalmic monitoring processes or other procedures. In such an embodiment, the lens may be manufactured from a hydrophilic material of the type used to manufacture soft contact lenses, or the lens may be manufactured from polymethylmethacrylate ("PMMA") and ensheathed in a hydrophilic material of the type used to manufacture soft contact lenses. Alternatively, a lens in accordance with the present invention might be placed over a bandage lens, such as a soft contact lens.

Accordingly, it is an object of the present invention to provide a scleral contact lens that may be worn by a patient for substantial periods of time, may be manipulated easily and may hold a patient's eyelid open during pupil or retina monitoring procedures.

It is another object of the present invention to provide an improved corneal contact lens for use in pupil or retina monitoring procedures.

DESCRIPTION OF PREFERRED EMBODIMENTS

Figure 1:
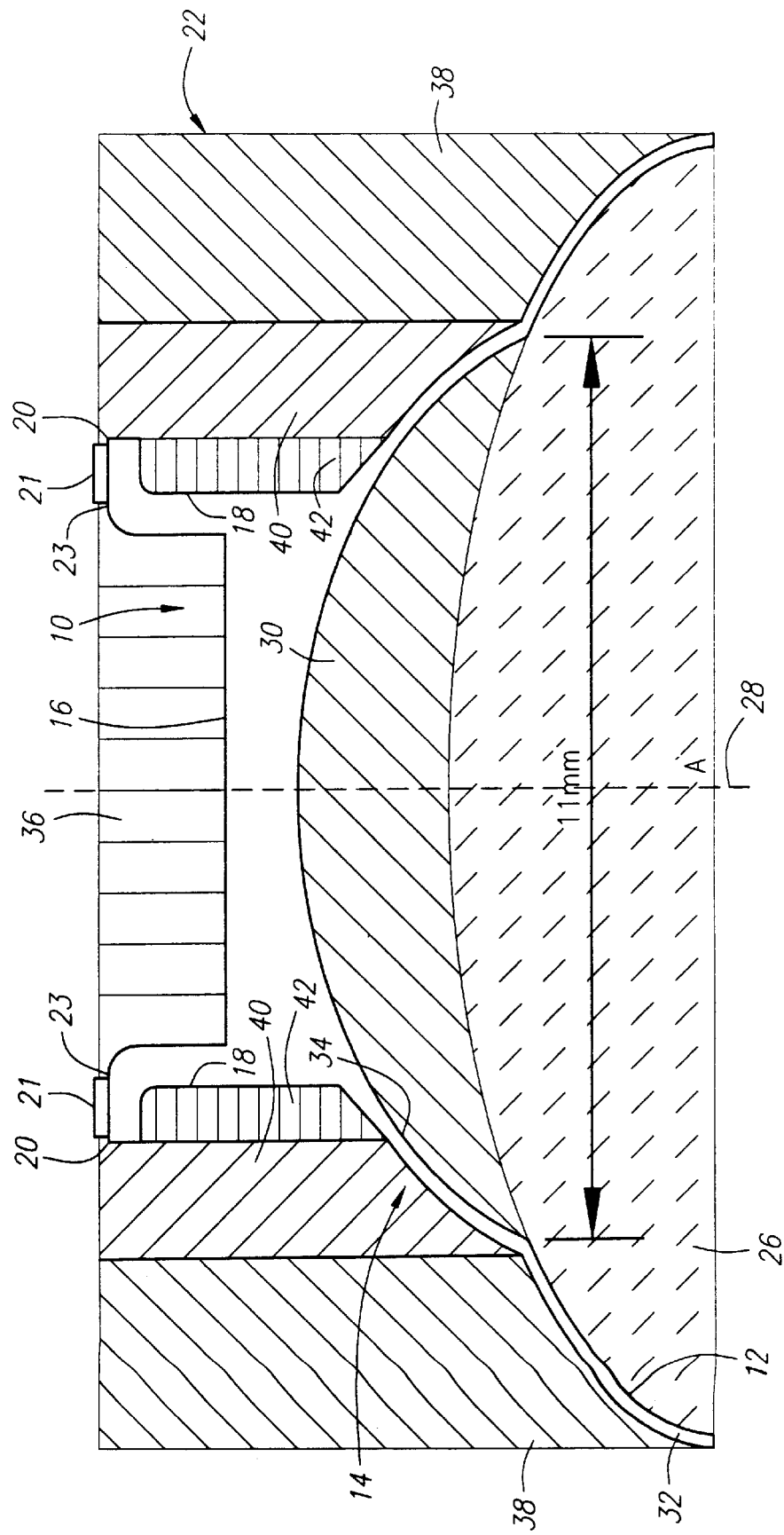
FIG. 1 is an illustration of a scleral contact lens in accordance with one preferred form of the present invention.

Turning now to the drawings, FIG. 1 illustrates a scleral contact lens 10 in accordance with the present invention, and illustrates how such a lens may be cut, for example, from a cylindrical block of polymethylmethacrylate ("PMMA"), polyhema, itafluorofocon B or flurosiliconacrylate. As shown, the scleral contact lens 10 has a back surface 12 that conforms to the cornea and sclera (not shown) of a patient's eye, and a front surface 14 whereon a viewing port 16 is provided. In a preferred form, the portion of the back surface 12 that conforms to the sclera of a patient's eye is adapted to rest on the sclera, while the portion of the back surface 12 that conforms to the cornea is slightly separated from the cornea. In alternative forms, the portion of the back surface 12 that conforms to the cornea of a patient's eye may also rest on the cornea. The viewing port 16 is formed within a tubular extension 18 that extends outwardly from the front surface 14 of the scleral contact lens 10. A distal portion of the tubular extension 18 that surrounds the viewing port 16 forms an outwardly protruding lip 20. The outwardly protruding lip 20 functions to hold the eyelid of a patient open during, for example, a pupil or retina monitoring process, and facilitates manipulation of the scleral contact lens 10 while it is being inserted in or removed from the patient's eye. In addition, the provision of the outwardly protruding lip 20 enables the length of the tubular extension 18 to be minimized, thus, maximizing the utility of the viewing port 16. The viewing port 16 permits clear, unobstructed viewing of the iris, pupil and/or retina of a patient's eye through the cornea.

In a presently preferred form, a plurality of fiduciary points 21 may be provided along an upper surface 23 of the outwardly protruding lip 20, and may be used as a means for calibrating an associated ophthalmic monitoring system, providing a three dimensional location of the lens and/or determining an amount of rotation of an eye during, for example, pupil or pulse oximetry monitoring processes. The fiduciary points 21 may take numerous forms including, for example, colored shapes or textured areas. By comparing observed areas of the fiduciary points 21 during a monitoring process it is possible to determine a degree of rotation of an eye during the monitoring process.

The scleral contact lens 10 may be formed by milling, for example, a cylindrical block 22 of polymethylmethacrylate (PMMA), polyhema, itafluorofocon B or flurosiliconacrylate that has been mounted on a lathe (not shown). However, those skilled in the art will appreciate that other materials may also be used without departing in any significant manner from the disclosures herein. To form the back surface 12 of the scleral contact lens 10, a first semi-spherical section 26 centered on the cylindrical axis 28 of the scleral contact lens 10 may be removed from the cylindrical block 22. In a preferred form, the radius of curvature of the first semi-spherical section 26 may conform to the radius of curvature of the sclera of a patient's eye. After the first semi-spherical region 26 has been removed, a second semi-spherical region 30 also centered on the cylindrical axis 28 may be removed from the cylindrical block 22. The radius of curvature of the second semi-spherical section 30 may conform to the radius of curvature of the cornea of the patient's eye. Typically, the radius of curvature of the first section 26 may range from 6–8 mm, with 7 mm being preferred, and the radius of curvature of the second section may range from 10–12 mm, with 11 mm being preferred. Thus, it will be noted by those skilled in the art that the removal of the first section 26 defines a scleral flange 32, and the removal of the second section 30 may define a corneal recess 34 in the back surface 12 of the scleral contact lens 10.

The front surface 14 of the scleral contact lens 10 may be formed by first removing a cylindrical section 36 centered on the cylindrical axis 28 of the scleral contact lens 10. The diameter of the removed cylindrical section 36 may range from 8 to 15 mm, and 11 mm is presently preferred. Additional sections 38, 40, and 42 may then be removed from the perimeter of the cylindrical block 22, so as to shape the remainder of the front surface 14 of the scleral contact lens 10. The dimensions of section 42 and, accordingly, the dimensions of the lip portion 20 of the tubular extension 18 are preferably determined to ensure that the eyelid of a patient will not ride over the tubular extension 18 during the monitoring process, thus maintaining a clear optical path for viewing the iris, pupil and retina during that process. Moreover, it will be noted that by providing the lip 20 it is possible to minimize the height of the tubular extension 18, and to maximize the viewing area of the lens 10. Those skilled in the art will appreciate that, when manufacturing a contact lens in accordance with the present invention, it may also be desirable to build or mold the contact lens body and tubular extension 18 as separate units and, thereafter, attach the tubular extension 18 to the lens body.

Figure 2A:
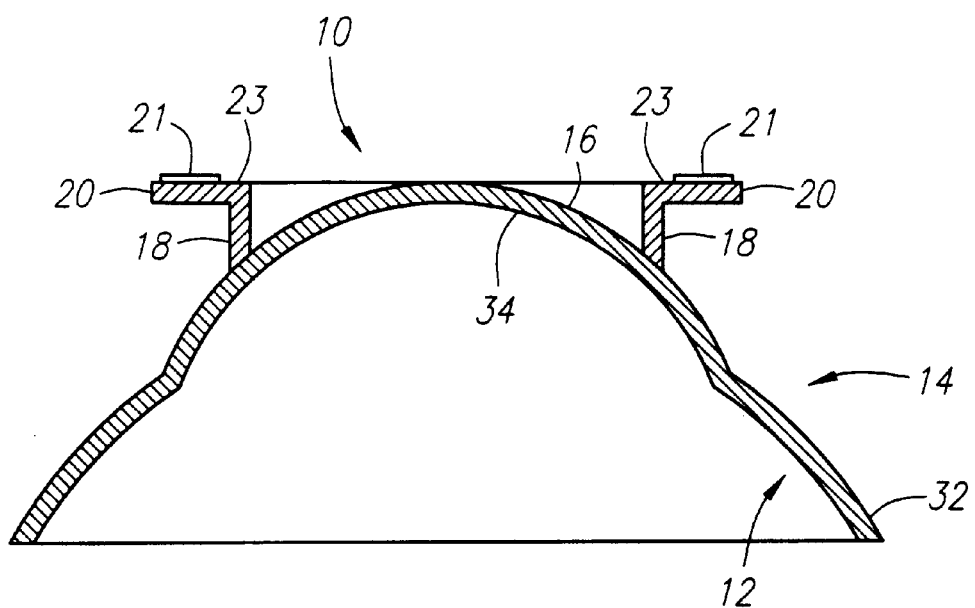
FIGS. 2(a) and 2(b) illustrate the dimensions of exemplary scleral contact lenses in accordance with the present invention.
Figure 2B:
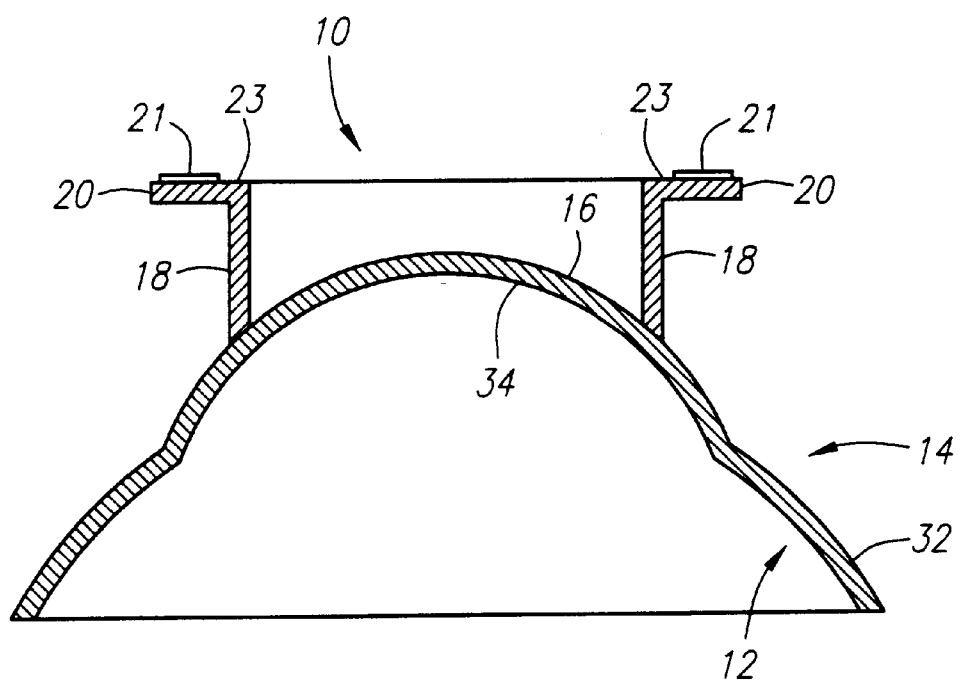
Figure 3:
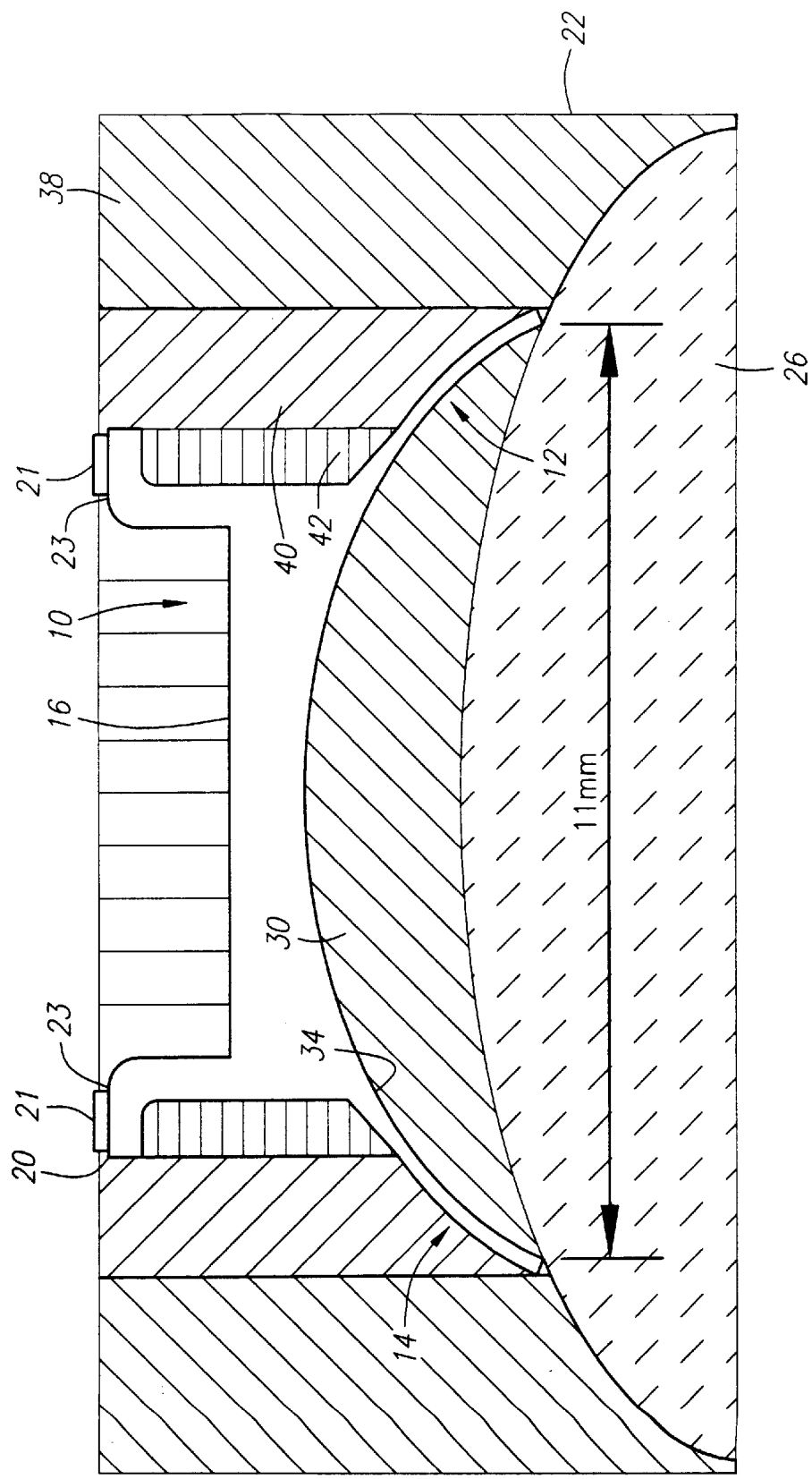
FIG. 3 is an illustration of a corneal contact lens in accordance with a second preferred form of the present invention.

Exemplary dimensions of a scleral contact lens 10 in accordance with the present invention are shown in FIGS. 2(a) and 2(b), and an alternative embodiment of a contact lens designed to cover only the cornea of a patient's eye is shown in FIG. 3.

Figure 4:
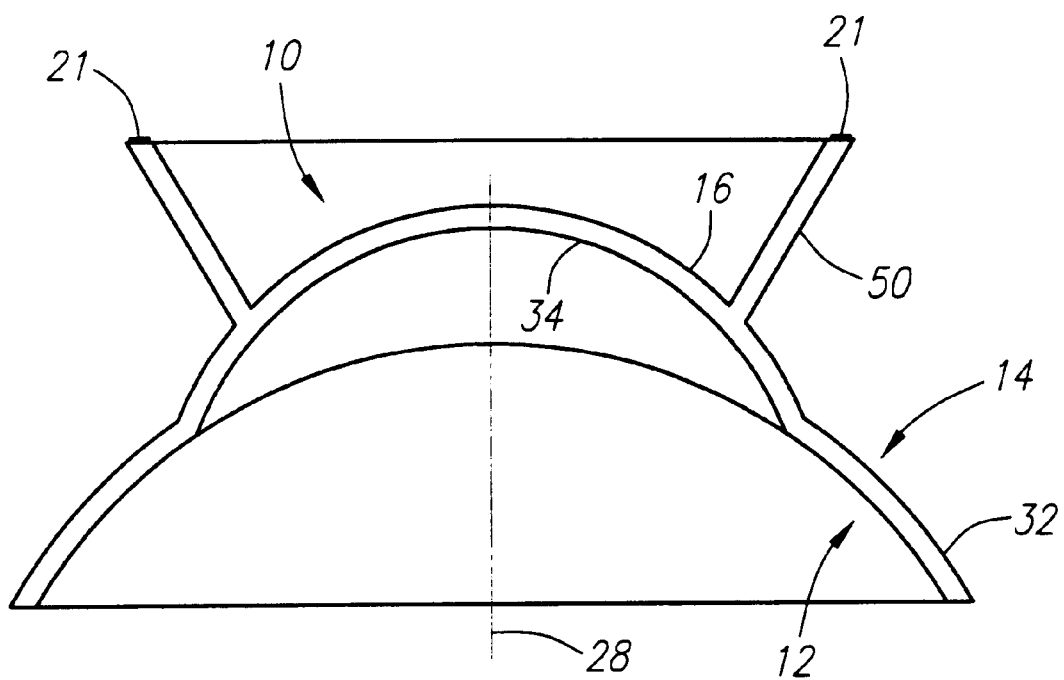
FIG. 4 is an illustration of a contact lens having a flared tubular extension in accordance with a third preferred form of the present invention.

Turning now to FIG. 4, for some applications it may be desirable to utilize a contact lens 10 having a flared tubular extension 50 for holding the eyelid (not shown) of a patient open during ophthalmic monitoring processes, as such an extension may provide increased visibility of the vessels and other structures within the eye.

It will be noted by those skilled in the art that scleral contact lenses 10 in accordance with the present invention may be made from any of a number of substances including, for example, polymethylmethacrylate (PMMA), polyhema, itafluorofocon B, flurosiliconacrylate, or any of the materials currently used to manufacture soft contact lenses including, for example, etafilcon, bufilcon A, phemfilcon and polybuthylbuthylacrylate. In addition, it will be noted that a scleral contact lens 10 in accordance with the present invention may comprise a hard lens material, such as polymethylmethacrylate (PMMA), polybuthy$^2$bethacrylate or itafluorofocon B, and a soft material such as etafilcon. In such an embodiment, the soft material may be provided solely on the back surface 12 of the scleral contact lens 10, or it may ensheathe a substantial portion of the scleral contact lens 10.

Finally, in still another embodiment, the viewing port 16 may comprise or include a wide angle lens (not shown), a polarizing lens or film (not shown) or some other type of optical filtering device or material. The manufacture of such lens structures and materials is well known in the art and, thus, is not described herein.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A scleral contact lens comprising:
   a lens body and a scleral flange,
   said scleral flange surrounding and extending outwardly from a perimeter region of said lens body, and
   said lens body having a back surface and a front surface, said back surface having a curved region for receiving a cornea of an eye, and said front surface comprising a viewing port through which the eye can be viewed during a monitoring process, said viewing port being surrounded by a raised tubular extension that extends outwardly from the front surface of the contact lens, said raised tubular extension having an outwardly protruding distal lip region for engaging an eyelid and preventing said eyelid from passing over said viewing port, wherein said distal lip region lies substantially perpendicular to a distal end of the raised tubular extension and enables a length of the tubular extension to be reduced, thus increasing the utility of the viewing port.

2. The scleral contact lens of claim 1, wherein said lens body and said scleral flange are manufactured from polymethylmethacrylate (PMMA) or itafluorofocon B.

3. The scleral contact lens of claim 1, wherein said lens body and scleral flange are manufactured from polyhema.

4. The scleral contact lens of claim 1, wherein said scleral flange and said back surface of said lens body are manufactured from a substance selected from a group of etafilcon, bufilcon A, polybuthylbuthylacrylate and phemfilcon, and said front surface of said lens body is manufactured from a substance selected from the group of polymethylmethacrylate, itafluorofocon B, polyhema and flurosiliconacrylate.

5. The scleral contact lens of claim 1, wherein a wide angle lens is provided in said viewing port.

6. A contact lens comprising:

a lens body having a back surface and a front surface, said back surface having a curved region for receiving a cornea of an eye, said front surface comprising a viewing port through which the eye can be viewed during a monitoring process, said viewing port being surrounded by a raised tubular extension that extends outwardly from the front surface of the contact lens, and said raised tubular extension having an outwardly protruding distal lip region for engaging an eyelid and preventing said eyelid from passing over said viewing port, wherein said distal lip region lies substantially perpendicular to a distal end of the raised tubular extension, and enables a length of the tubular extension to be reduced, thus increasing the utility of the viewing port.

7. The contact lens of claim 6, wherein said lens body is manufactured from a substance selected from a group of polymethylmethacrylate (PMMA), itafluorofocon B, polyhema and flurosiliconacrylate.

8. The contact lens of claim 6, wherein said lens body is manufactured from a substance selected from a group of etafilcon, bufilcon A, phemfilcon and polybuthylbuthylacrylate.

9. The contact lens of claim 6, wherein said back surface of said lens body is manufactured from a substance from a group of etafilcon, bufilcon A, phemfilcon and polybuthylbuthylacrylate, and said front surface of said lens body is manufactured from a material selected from a group of polymethylmethacrylate, itafluorofocon B, polyhema and flurosiliconacrylate.

10. The contact lens of claim 6, wherein a wide angle lens is provided in said viewing port.

11. A contact lens comprising:

a lens body having a back surface and a front surface, said back surface having a curved region for receiving a cornea of an eye, said front surface comprising a viewing port through which the eye can be viewed during a monitoring process, said viewing port being surrounded by a raised tubular extension that extends outwardly from the front surface of the contact lens, and said raised tubular extension with an outwardly protruding lip for engaging an eyelid and preventing said eyelid from passing over said viewing port, wherein an under-side surface of said outwardly protruding lip lies substantially perpendicular to a distal end of said raised tubular extension.

12. The contact lens of claim 11, wherein said lens body is manufactured from a substance selected from a group of polymethylmethacrylate (PMMA), itafluorofocon B, polyhema and flurosiliconacrylate.

13. The contact lens of claim 11, wherein said lens body is manufactured from a substance selected from a group of etafilcon, bufilcon A, phemfilcon and polybuthylbuthylacrylate.

14. The contact lens of claim 11, wherein said back surface of said lens body is manufactured from a substance selected from a group of etafilcon, bufilcon A, phemfilcon and polybuthylbuthylacrylate, and said front surface of said lens body is manufactured from a material selected from a group of polymethylmethacrylate, itafluorofocon B, polyhema and flurosiliconacrylate.

15. The contact lens of claim 11, wherein a wide angle lens is provided in said viewing port.

* * * * *